United States Patent
Huff et al.

(10) Patent No.: US 9,615,927 B2
(45) Date of Patent: Apr. 11, 2017

(54) ORTHOPAEDIC SURGICAL INSTRUMENT SYSTEM AND METHOD FOR PROTECTING A FEMORAL STEM TAPER

(71) Applicant: DEPUY IRELAND UNLIMITED COMPANY, Co Cork OT (IE)

(72) Inventors: Daniel N. Huff, Warsaw, IN (US); Justin D. Grostefon, Columbia City, IN (US)

(73) Assignee: DEPUY IRELAND UNLIMITED COMPANY, Co Cork (IE)

( * ) Notice: Subject to any disclaimer, the term of this patent is extended or adjusted under 35 U.S.C. 154(b) by 0 days.

(21) Appl. No.: 14/675,389

(22) Filed: Mar. 31, 2015

(65) Prior Publication Data

US 2016/0287396 A1    Oct. 6, 2016

(51) Int. Cl.
*A61F 2/36*  (2006.01)
*A61F 2/46*  (2006.01)
*A61F 2/30*  (2006.01)

(52) U.S. Cl.
CPC .......... *A61F 2/3609* (2013.01); *A61F 2/4607* (2013.01); *A61F 2/4637* (2013.01); *A61F 2002/30067* (2013.01); *A61F 2002/30718* (2013.01); *A61F 2002/3611* (2013.01); *A61F 2002/3625* (2013.01); *A61F 2002/4641* (2013.01)

(58) Field of Classification Search
CPC .. A61F 2/3609; A61F 2/36; A61F 2/46; A61F 2/3611; A61F 2002/3625; A61F 2002/365; A61F 2002/3652; A61B 17/1742
USPC ................ 623/22.12, 23.13, 23.21
See application file for complete search history.

(56) References Cited

U.S. PATENT DOCUMENTS

| | | | | |
|---|---|---|---|---|
| 3,801,989 A | * | 4/1974 | McKee | A61F 2/32 606/86 R |
| 3,818,514 A | * | 6/1974 | Clark | A61F 2/3609 206/438 |
| 4,993,410 A | * | 2/1991 | Kimsey | A61F 2/4607 606/100 |
| 5,133,765 A | * | 7/1992 | Cuilleron | A61F 2/0095 206/363 |

(Continued)

FOREIGN PATENT DOCUMENTS

| | | |
|---|---|---|
| EP | 0207873 | 1/1987 |
| GB | 2042897 | 10/1980 |

OTHER PUBLICATIONS

International Search Report, PCT/US2016/024852, Mar. 30, 2016, 6 pages.

*Primary Examiner* — Alvin Stewart
(74) *Attorney, Agent, or Firm* — Barnes & Thornburg LLP (57) ABSTRACT

An orthopaedic hip prosthesis system is disclosed. The orthopaedic hip prosthesis system comprises a femoral head component configured to articulate with a natural or prosthetic acetabulum of a patient, the femoral head component having a tapered bore formed therein, a femoral stem component having a tapered trunnion configured to be received in the tapered bore of the femoral head component, and a shell positioned over the tapered trunnion of the femoral stem component. The shell includes a frame extending over the tapered trunnion, and a protective coating applied to the frame and the tapered trunnion. A method of performing an orthopaedic surgery is also disclosed.

20 Claims, 8 Drawing Sheets

(56) References Cited

U.S. PATENT DOCUMENTS

| | | | | |
|---|---|---|---|---|
| 5,147,366 | A * | 9/1992 | Arroyo | A61B 17/8808 606/92 |
| 5,405,394 | A * | 4/1995 | Davidson | A61L 27/306 623/18.11 |
| 5,674,225 | A * | 10/1997 | Muller | A61B 17/1659 606/100 |
| 5,735,905 | A * | 4/1998 | Parr | A61F 2/3609 623/23.11 |
| 5,865,850 | A * | 2/1999 | Matthews | A61F 2/3609 623/22.43 |
| 5,885,295 | A * | 3/1999 | McDaniel | A61B 17/8802 606/85 |
| 6,110,179 | A * | 8/2000 | Flivik | A61B 17/8808 606/94 |
| 6,344,060 | B1 * | 2/2002 | Schmotzer | A61F 2/30724 606/95 |
| 6,585,771 | B1 * | 7/2003 | Buttermilch | A61B 90/94 623/21.11 |
| 6,669,734 | B2 * | 12/2003 | Spotorno | A61F 2/30724 623/23.15 |
| 6,797,007 | B1 * | 9/2004 | Von Chamier | A61F 2/34 623/22.45 |
| 7,879,042 | B2 * | 2/2011 | Long | A61F 2/4607 606/99 |
| 8,361,162 | B2 * | 1/2013 | Berry | A61F 2/30724 623/22.12 |
| 9,248,021 | B1 * | 2/2016 | Termanini | A61F 2/30721 |
| 2002/0052661 | A1 | 5/2002 | Spotorno | |
| 2004/0015238 | A1 * | 1/2004 | Buehler | A61B 17/8808 623/22.12 |
| 2004/0143340 | A1 * | 7/2004 | Tuma | A61F 2/4657 623/22.12 |
| 2006/0167557 | A1 * | 7/2006 | Terrill | A61F 2/3609 623/22.43 |
| 2007/0100464 | A1 | 5/2007 | Meulink | |
| 2009/0299484 | A1 * | 12/2009 | Dietrich | A61F 2/0095 623/22.4 |
| 2010/0241239 | A1 | 9/2010 | Smith | |
| 2014/0094927 | A1 * | 4/2014 | Weeden | A61F 2/32 623/22.21 |
| 2015/0216667 | A1 * | 8/2015 | Monaghan | A61F 2/30 623/23.42 |
| 2015/0272740 | A1 * | 10/2015 | Wakiyama | A61F 2/3609 623/23.11 |
| 2016/0074167 | A1 * | 3/2016 | Vautrin | A61F 2/30942 623/23.52 |

\* cited by examiner

ORTHOPAEDIC SURGICAL INSTRUMENT SYSTEM AND METHOD FOR PROTECTING A FEMORAL STEM TAPER

TECHNICAL FIELD

The present disclosure relates generally to orthopaedic hip prostheses and, more particularly, to surgical systems used to protect a femoral stem component of an orthopaedic hip prosthesis.

BACKGROUND

Joint arthroplasty is a well-known surgical procedure by which a diseased or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes a stem component that is received in the medullary canal of the patient's femur and a spherically-shaped head component that bears against the patient's acetabulum or a prosthetic replacement acetabular cup.

The elongated stem implant may be cemented into the medullary canal or may have a surface conducive for allowing the bone to heal directly to the implant. In some prostheses, the head component is attached to a neck of the stem component via a tapered trunnion. The acetabulum of the patient may also be reamed to receive a shell and a liner. A polyethylene, metal or ceramic liner with a metal shell is inserted into the acetabulum and acts as a socket for receiving the head component.

SUMMARY

According to one aspect of the disclosure, an orthopaedic hip prosthesis system is disclosed. The orthopaedic hip prosthesis system comprises a femoral head component configured to articulate with a natural or prosthetic acetabulum of a patient, the femoral head component having a tapered bore formed therein, a femoral stem component having a tapered trunnion configured to be received in the tapered bore of the femoral head component, and a shell positioned over the tapered trunnion of the femoral stem component. The shell includes a frame extending over the tapered trunnion, and a protective coating applied to the frame and the tapered trunnion.

In some embodiments, the femoral stem component may include an elongated body extending to a distal tip and a neck extending superiorly and medially from a proximal end of the elongated body, and the tapered trunnion extends from the proximal end of the neck.

In some embodiments, the tapered trunnion may include a tapered outer surface that extends from a proximal surface to a distal edge connected to the proximal end of the neck, and the shell extends over the entire tapered outer surface.

In some embodiments, the frame may be formed from a first material and the protective coating is formed from a second material different from the first material.

In some embodiments, the first material may be a plastic.

In some embodiments, the second material may be a biocompatible wax.

In some embodiments, the frame may be a unitary plastic body shaped to conform to the tapered trunnion.

In some embodiments, the body of the frame may comprise a base configured to engage a proximal surface of the tapered trunnion, and a plurality of arms extending from the base along a tapered outer surface of the tapered trunnion.

In some embodiments, the shell may further include a tab extending outwardly from a distal end of each arm away from the tapered trunnion.

In some embodiments, the protective coating may completely cover the base and the plurality of arms of the frame.

In some embodiments, the orthopaedic prosthesis may include a surgical instrument configured to detach the shell from the tapered trunnion of the femoral stem component, the surgical instrument including a cavity sized to receive the tapered trunnion with the shell positioned thereon, and a collar adapted to engage a distal end of the shell to detach the shell from the tapered trunnion.

In some embodiments, the shell may include one or more tabs extending away from the tapered trunnion, and the collar is configured to engage the one or more tabs when the tapered trunnion and the shell are positioned in the cavity.

In some embodiments, the collar may be configured to deflect the shell outwardly from the tapered trunnion when the surgical instrument is pulled away from the tapered trunnion.

According to another aspect, a system for hip orthopaedic surgery is disclosed. The system may include a femoral head component configured to articulate with a natural or prosthetic acetabulum of a patient, the femoral head component having a tapered bore formed therein, a femoral stem component having a tapered trunnion configured to be received in the tapered bore of the femoral head component, the tapered trunnion defining a longitudinal axis, a shell positioned over the tapered trunnion of the femoral stem component. The shell may include a frame extending over the tapered trunnion, one or more distal tabs extending from the frame away from the tapered trunnion, and a protective coating applied to the frame and the tapered trunnion, and a surgical instrument configured to detach the shell from the tapered trunnion of the femoral stem component, the surgical instrument including a cavity sized to receive the tapered trunnion with the shell positioned thereon, and a collar adapted to engage the one or more distal tabs of the shell to detach the shell from the tapered trunnion. When the surgical instrument is advanced in a first direction along the longitudinal axis of the tapered trunnion, engagement between the collar and the one or more distal tabs of the frame causes the one or more distal tabs to deflect inwardly as the tapered trunnion and the shell are advanced into the cavity, and when the surgical instrument is advanced in a second direction opposite the first direction when the tapered trunnion and the shell are positioned in the cavity, the engagement between the collar and the one or more distal tabs causes the shell to deflect outwardly and detach from the tapered trunnion.

In some embodiments, the femoral stem component may include an elongated body extending to a distal tip and a neck extending superiorly and medially from a proximal end of the elongated body, and the tapered trunnion extends from the proximal end of the neck.

In some embodiments, the tapered trunnion may include a tapered outer surface that extends from a proximal tip to a distal edge connected to the proximal end of the neck, and the shell extends over the entire tapered outer surface.

In some embodiments, the frame of the shell may comprise a base configured to engage a proximal surface of the tapered trunnion, and a plurality of arms extending from the base along a tapered outer surface of the tapered trunnion to corresponding distal ends, and the one or more tabs extend from the distal ends of the plurality of arms.

In some embodiments, the frame may be a unitary plastic body shaped to conform to the tapered trunnion.

In some embodiments, the protective coating may be formed from a biocompatible wax.

According to another aspect, a method of performing an orthopaedic surgical procedure is disclosed. The method may include selecting an orthopaedic hip prosthesis that comprises a femoral stem component including a tapered trunnion sized to be received in a tapered bore of a femoral head component and a shell positioned over the tapered trunnion of the femoral stem component, the shell includes a frame extending over the tapered trunnion, one or more distal tabs extending from the frame away from the tapered trunnion, and a protective coating applied to the frame and the tapered trunnion, inserting the femoral stem component into a proximal end of a patient's femur, advancing a surgical instrument over the tapered trunnion and the shell, engaging a collar of the surgical instrument with the one or more distal tabs to deflect the one or more distal tabs inwardly toward the femoral stem component, pulling the surgical instrument away from the femoral stem component such that the engagement between the collar of the surgical instrument and the one or more distal tabs causes the shell to deflect outwardly and detach from the tapered trunnion, and securing the femoral head component to the tapered trunnion of the femoral stem component.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
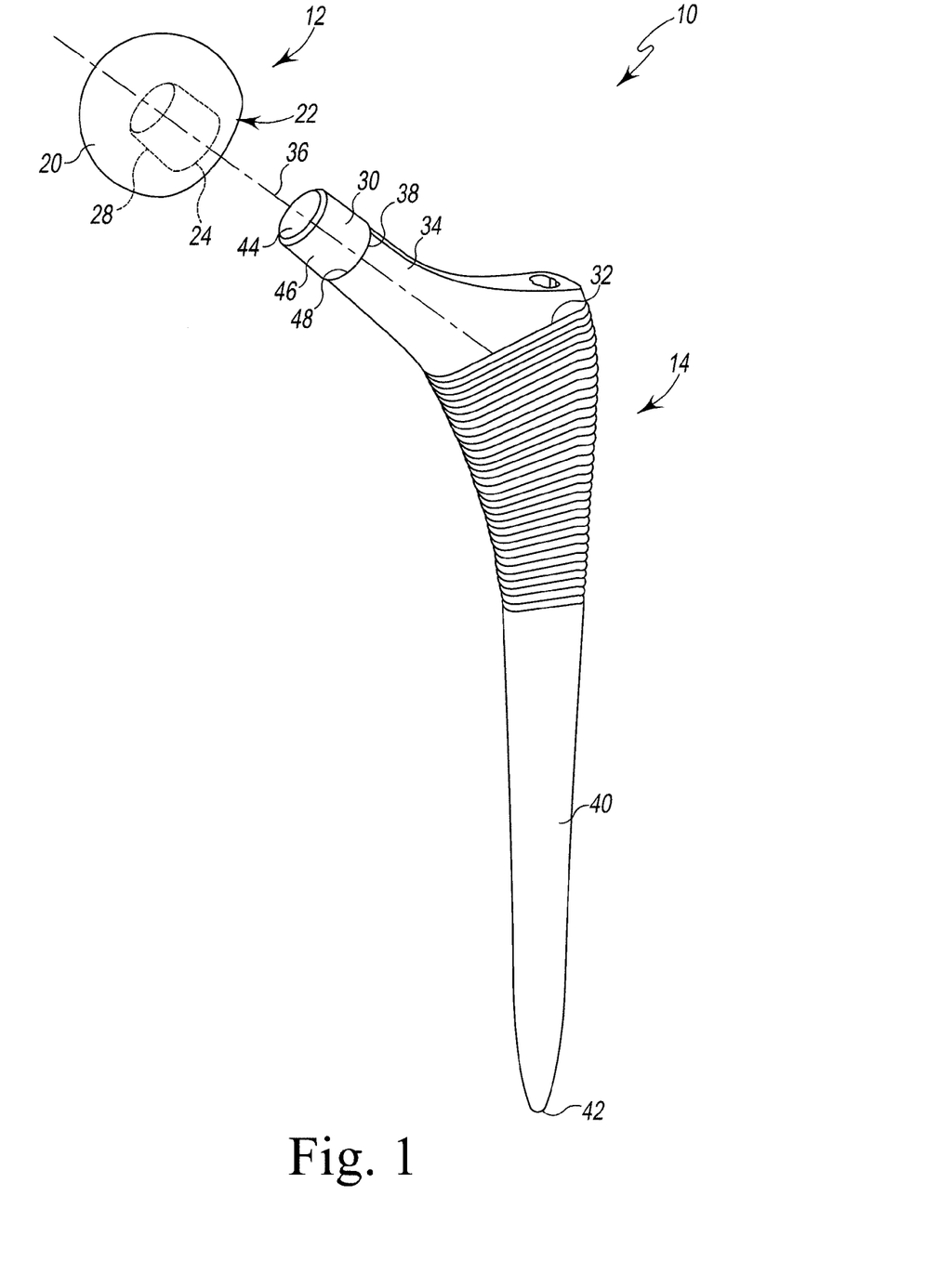
FIG. 1 is an exploded perspective view of an embodiment of a hip prosthesis including a tapered stem and a femoral ball.
Figure 2A:
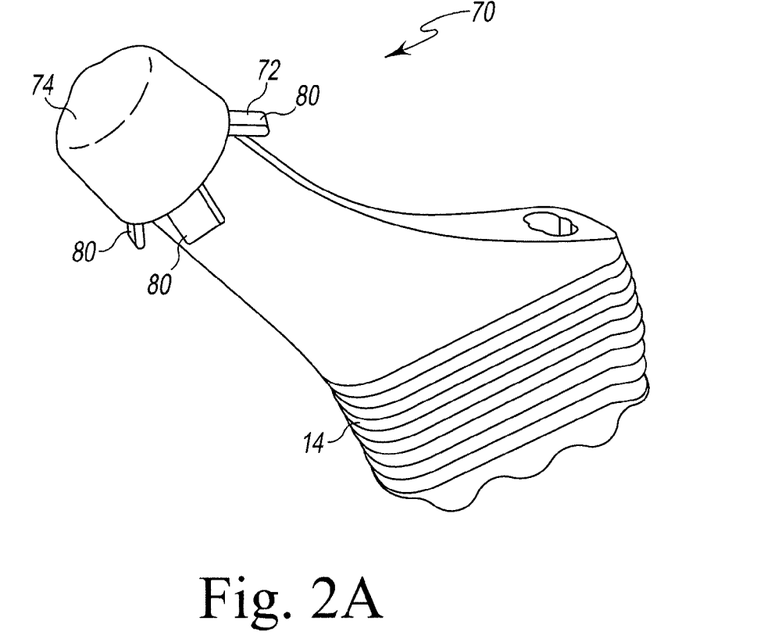
FIGS. 2A-2B is a perspective view of the stem of FIG. 1 with a protective layer, which is part of a taper protection system.
Figure 2B:
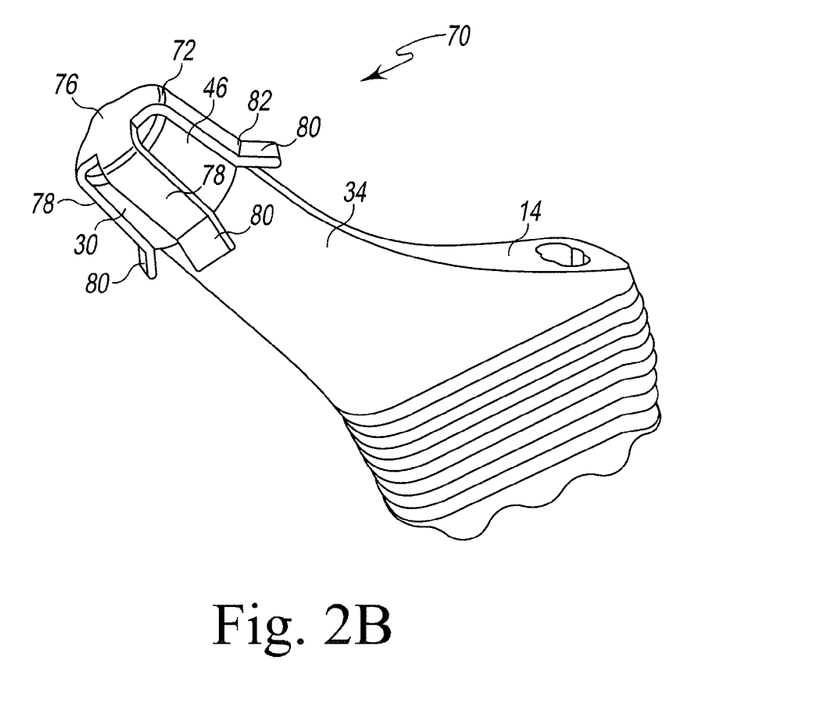

Referring to FIGS. 1-2B, an orthopaedic prosthesis is illustratively embodied as a femoral orthopaedic implant 10 of a hip prosthesis. The femoral orthopaedic implant 10 (hereinafter implant 10) includes a head component 12 and a stem component 14 that is configured to be inserted into an intramedullary canal 16 of a patient's surgically-prepared femur 18. In particular, the femoral stem component 14 is implanted into a surgically prepared (e.g., broached) intramedullary canal 16 of the patient's femur 18.

As described in greater detail below, the femoral stem component 14 may be implanted into the patient with a protective shell 70 in place over the trunnion 30, thereby protecting the trunnion 30 from damage and undesired fluid contact during surgery. When the surgeon is ready to attach the head component 12 to the femoral stem component 14, a surgical tool 150 (see FIG. 5) may be used to remove the shell 70 from the trunnion 30, revealing a clean, dry trunnion 30 to receive the head component 12. As will be discussed in more detail below, the shell 70 cooperates with the removal tool 150 to allow the surgeon to effectively and quickly remove the protective shell 70 from the stem component 14.

The head component 12 includes a spherical outer surface 20 configured to engage a patient's natural acetabulum (not shown) or a prosthetic acetabular cup implanted into the patient's pelvic bone. The head component 12 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. The head component 12 also includes a distal surface 22 having an opening 24 defined therein, and an inner wall extends inwardly from the opening 24 to define a tapered bore 28 in the head component 12.

The head component 12 is secured to a trunnion 30 formed at a proximal end 32 of the elongated neck 34 of the stem component 14. As shown in FIG. 1, the elongated neck 34 has a longitudinal axis 36 that extends through the trunnion 30. In the illustrative embodiment, the head component 12 is advanced along the longitudinal axis 36, such that the tapered trunnion 30 of the stem component 14 enters the tapered bore 28 of the head component 12 and taper locks the trunnion 30 (and hence the stem component 14) and the femoral head component 12 to one another. When installed on the stem component 14, the femoral head component 12 is positioned to bear on either the patient's natural acetabulum or a prosthetic socket which has been implanted into the patient's pelvis to replace his or her acetabulum. In such a manner, the orthopaedic hip prosthesis 10 and the natural or artificial acetabulum collectively function as a system which replaces the natural joint of the patient's hip.

As shown in FIG. 1, the elongated neck 34 extends medially and superiorly from a proximal end 38 of an elongated body 40 of the stem component 14. The elongated body 40 extends inferiorly and distally away from the proximal end 38 to a rounded distal tip 42 that defines the inferior-most surface of the femoral stem component 14. The elongated body 40 is sized to be received in an intramedullary canal of the patient's femur. In some embodiments, the elongated body 40 may be cemented or press-fit into the intramedullary canal of the patient.

The trunnion 30 extends from the proximal end 32 of the elongated neck 34 to a proximal surface 44 of the trunnion 30. The trunnion 30 includes a tapered outer surface 46 that extends from the proximal surface 44 to a distal edge 48 of the trunnion 30. The distal edge 48 is coupled to the proximal end 32 of the elongated neck 34.

In the illustrative embodiment described herein, the stem component 14 is embodied as a monolithic metal structure. The stem component 14 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic femoral stem component 14 may also be coated with a surface treatment, such as hydroxyapatite, to enhance biocompatibility. Moreover, the surfaces of the femoral stem component 14 that engage the natural bone, such as the outer surface of the elongated body 40, may be textured to facilitate securing the component to the bone. Such surfaces may also be porous coated to promote bone ingrowth for permanent fixation.

As shown in FIGS. 2A-2B, an illustrative embodiment of the femoral stem component 14 includes a protective shell 70 positioned over the tapered trunnion 30 to protect the tapered trunnion 30 from mechanical damage and undesired fluid contact during a joint arthroplasty. The shell 70 may include a frame 72 extending over the tapered trunnion 30 and a protective coating 74 applied to the frame 72 and the tapered trunnion 30.

Figure 3:
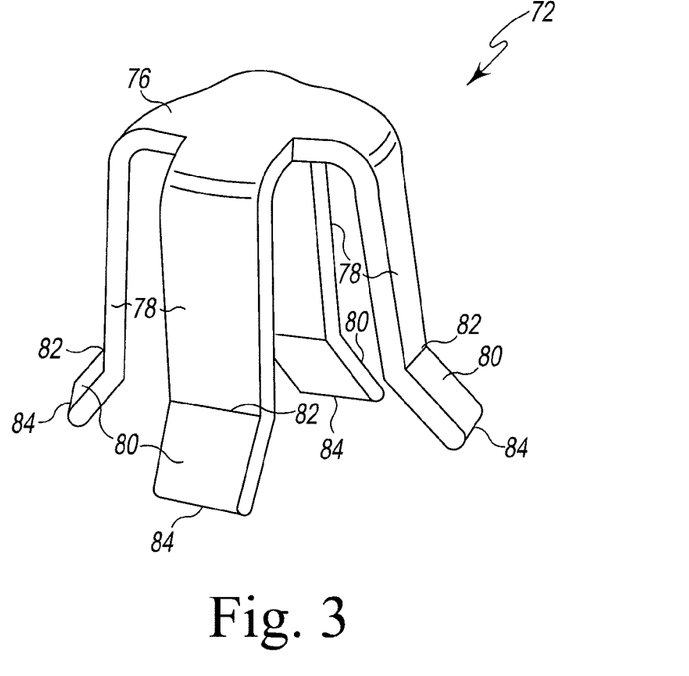
FIG. 3 is a perspective view of a frame of the taper protection system of FIG. 2.
Figure 4:
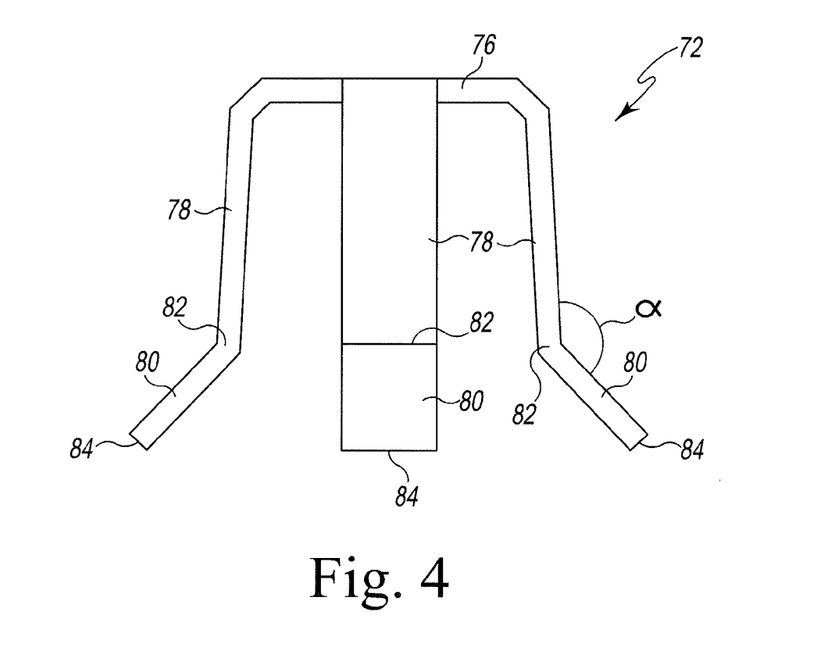
FIG. 4 is a side elevation view of the frame of FIG. 3.

As shown in FIGS. 3-4, the frame 72 is embodied as a single monolithic component shaped to conform to the tapered trunnion 30. The frame 72 may be constructed of a polymeric material, such as, for example, plastic, although other materials may be used. In the illustrative embodiment, the frame 72 is constructed of a material that does not cause mechanical damage to the stem component 14, e.g., the frame 72 does not scratch the stem component 14 as the frame 72 is advanced on or off of the trunnion 30.

The frame 72 includes a base 76 configured to engage the proximal surface 44 of the trunnion 30. A plurality of arms 78 extend from the base 76 and are configured to extend along the tapered outer surface 46 of the trunnion 30. The base 76 and the arms 78 are configured to conform to the shape of the trunnion 30. The frame 72 also includes a tab 80 extending outwardly from a distal tip 82 of each arm 78.

The tabs 80 are angled away from stem component 14 at a nonorthogonal angle (i.e., an angle other than 90 degrees). Similarly, the tabs 80 are also angled away from the arms 78 at a nonorthogonal angle. In the illustrative embodiment, the tabs 80 are angled away from the arms 78 at an angle α that is greater than ninety degrees. The tabs 80 are configured to interface with the removal tool 150 to facilitate the quick removal of the entire shell 70 from the stem component 14, including both the frame 72 and the protective coating 74. In the illustrative embodiment, the distal-most point of the shell 70 is one or more distal tips 84 of the tabs 80. The tabs 80 are angled away from the arms.

The arms 78 of the frame 72 are configured to extend along the outer surface 46 of the trunnion 30 from the proximal surface 44 of the trunnion 30 to the distal edge 48 of the trunnion 30. In such a configuration, the distal end 82 of each arm 78 is positioned to be near the distal edge 48 of the trunnion 30. Each tab 80 is angled outwardly (away from stem component 14) and distally along the length of the stem component 14, such that each tab 80 extends over the elongated neck 34. While the arms 78 conform to the shape of the stem component 14, the tabs 80 do not conform to the shape of the elongated neck 34. As shown in FIG. 3, the frame 72 includes four arms 78 extending from the base 76 and a single tab 80 extending from each arm 78. In some embodiments, the frame 72 may include any number of arms.

In the illustrative embodiment shown in FIG. 2, the protective coating 74 is embodied as a biocompatible wax, although other materials may be used. In some embodiments, the protective coating may be silicone. The protective coating 74 is configured to surround completely the trunnion 30, adhering to both the frame 72 and the stem component 14. The protective coating 74 cooperates with the frame 72 to provide an easy-to-remove barrier that protects the trunnion 30 during transport or during a joint arthroplasty surgery.

Biocompatible wax is useful as a protective coating because wax is solid at ambient temperatures, but, in many embodiments, has a low melting point (e.g., in some embodiments around 100 degrees Fahrenheit). Additionally, biocompatible wax is insoluble in water, thereby allowing it to provide a barrier to most fluids. In the illustrative embodiment, the protective coating 74 is applied to the stem component 14 by, first, positioning the frame 72 over the trunnion 30 and, second, applying the liquid biocompatible wax onto the trunnion 30 and the frame 72 (e.g., by coating or dipping). After the trunnion 30 and the frame 72 are removed from the liquid biocompatible wax, they will be encompassed in the liquid biocompatible wax. Once the biocompatible wax cools, it will form a solid barrier that is coupled to the trunnion 30 and the frame 72.

In the illustrative embodiment, the protective coating 74 completely surrounds of the trunnion 30, but surrounds only a portion of the frame 72 positioned on the trunnion 30. For example, the protective coating 74 may completely cover the base 76 and the plurality of arms 78 of the frame 72. At the same time, the protective coating 74 may extend from the proximal surface 44, along the outer surface 46, to the distal edge 48 of the trunnion 30. In the illustrative embodiment of the frame 72, the tabs 80 of the frame 72 extend past the distal edge 48 of the trunnion 30. Consequently, the tabs 80 may not contact the protective coating 74.

Figure 5:
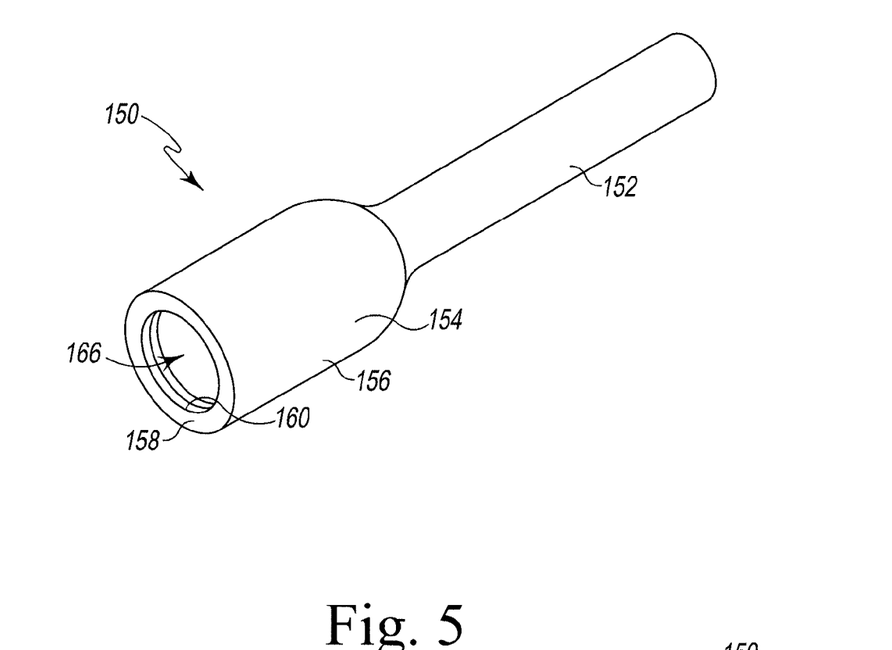
FIG. 5 is a perspective view of a removal tool of the taper protection system of FIG. 2.
Figure 6:
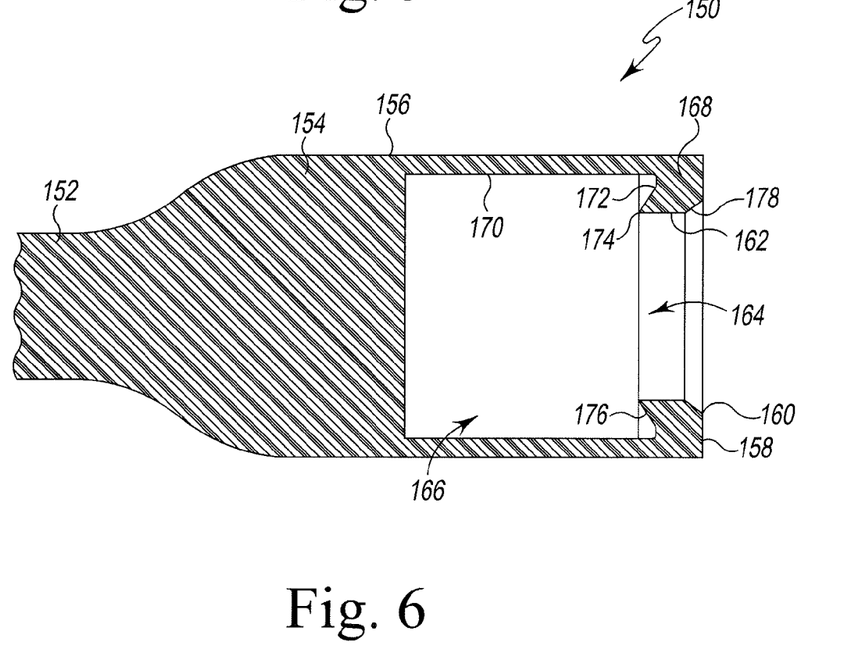
FIG. 6 is a cross-section view of the removal tool of FIG. 5 taken along the line 6-6.
Figure 7:
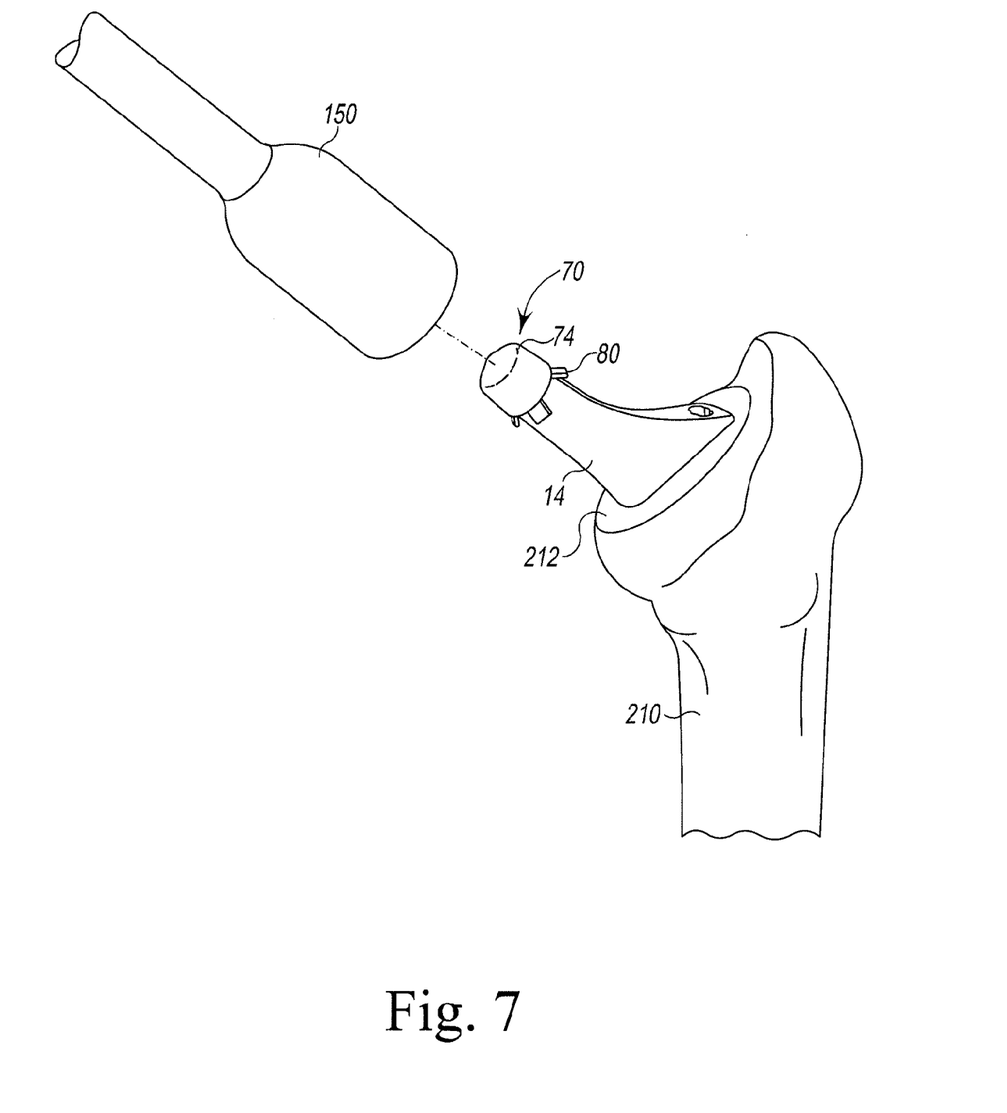
FIG. 7 is a perspective view of the taper protection system of FIG. 2 showing the tapered stem, the protective layer, and the removal tool.

As shown in FIGS. 5-6, a surgical removal tool 150 is configured remove the shell 70 from the trunnion 30 of the stem component 14. The removal tool 150 includes a handle 152 and a tool head 154 coupled to the handle 152. The tool head 154 has a cylindrical outer surface 156 and a distal surface 158 opposite the handle 152. An opening 160 is defined in the distal surface 158. An annular wall 162 extends inwardly from the opening 160 to define a passageway 164, which opens into a cylindrical cavity 166 formed in the interior of the tool head 154. The passageway 164 is sized to allow access to the cylindrical cavity 166, which is sized to receive the tapered trunnion 30 and the shell 70. The tool head 154 also includes a collar 168 configured to engage the tabs 80 of the protective shell 70, as described in greater detail below.

The annular wall 162 of the collar 168 defines the passageway 164 in the tool head 154. The annular wall 162 extends from the distal surface 158 of the tool head 154 to an inner edge 174 positioned in the cavity 166. In the illustrative embodiment, the opening 160 and the passageway 164 are sized such that the tabs 80 of the protective shell 70 will contact the annular wall 162 as the trunnion 30 with the protective shell 70 is advanced into the cavity 166 of the removal tool 150.

As shown in FIG. 6, the cavity 166 of the tool head 154 is defined by an inner cylindrical wall 170 that defines a diameter that is larger than the diameter of the opening 160. The collar 168 includes an inner wall 172 that extends inwardly from the inner cylindrical wall 170. In the illustrative embodiment, the collar 168 also includes a conical surface 176 that extends from the inner wall 172 to the inner edge 174. In use, the inner edge 174 and the conical surface 176 deflect the tabs 80 of the shell 70 outwardly, away from the stem component 14, as the trunnion 30 and the shell 70 are advanced out of the cavity 166. The tabs 80 are advanced into contact with the inner wall 172 of the inner wall 172, which cooperates with the inner cylindrical wall 170 to engage the deflected tabs 80 and cause the remaining parts of the shell 70 to deflect outwardly and detach from the tapered trunnion 30.

In the illustrative embodiment, the collar 168 includes a chamfer surface 178 that extends inwardly from the distal surface 158. The chamfer surface 178 is configured to deflect the tabs 80 of the shell 70 inwardly, toward the stem component 14, as the trunnion 30 and the shell 70 are advanced into the cavity 166 through the passageway 164. The chamfer surface 178 extends, at a non-orthogonal angle. The angle of the chamfer surface 178 compliments the angle of each tab 80 such that contact with the chamfer surface 178 causes the tabs 80 to deflect inwardly.

Referring now to FIGS. 7-11, an exemplary surgical procedure using the surgical tool 150 to remove a shell 70 from a stem component 14 is shown. In the illustrative embodiment, a reciprocating cutting saw or other cutting tool may be used to prepare a proximal end 212 of the patient's femur 210 to receive the stem component 14. A surgeon or other user may select an orthopaedic hip prosthesis from a number of orthopaedic hip prostheses of different sizes. After selecting the orthopaedic implant 10, the rounded distal tip 42 of the stem component 14 is inserted into the intramedullary canal of the patient's femur 210, and the stem component 14 is advanced into the intramedullary canal.

Figure 8:
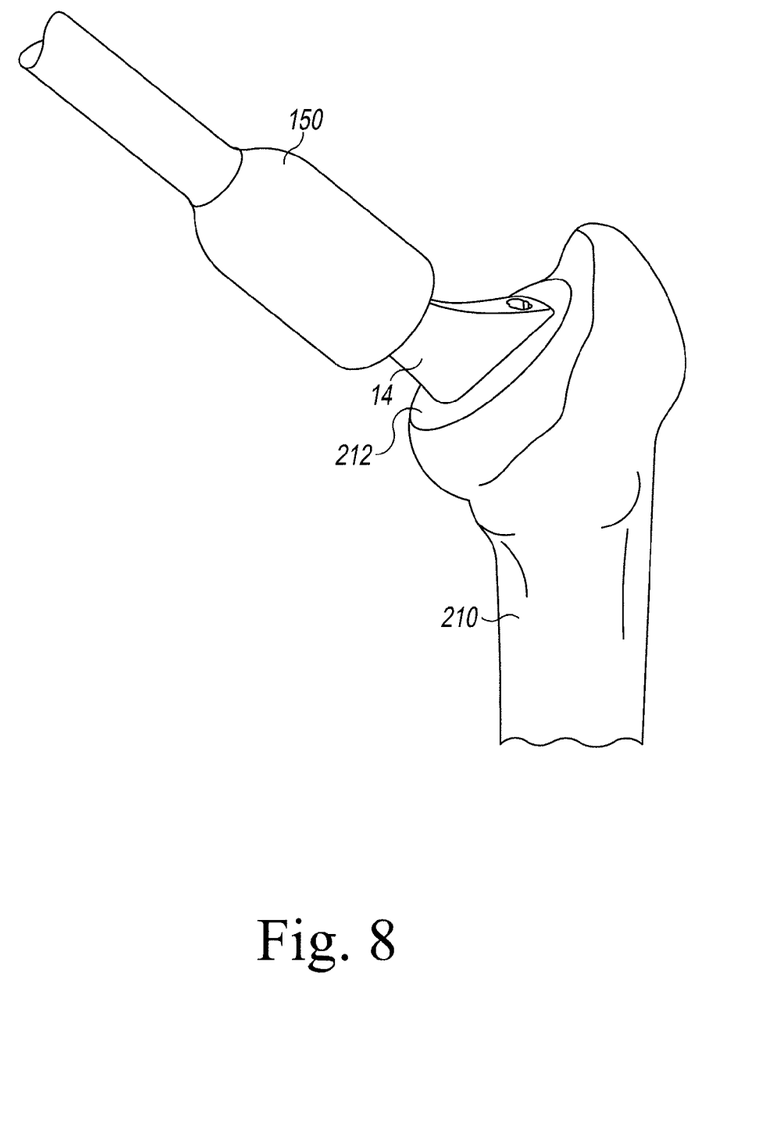
FIG. 8 is a perspective view of the taper protection system of FIG. 2 showing the femoral component inserted into the removal tool.

With the orthopaedic implant 10 positioned in the femur 210, the surgeon may advance the surgical instrument 150 over the tapered trunnion 30 and the shell 70, as shown in FIG. 8. Because the tabs 80 of the shell 70 define a diameter greater than the opening 160 of the removal tool 150, the tabs 80 are deflected inwardly by the chamfer surface 178 of the removal tool 150 as the surgeon advances the removal tool 150 onto the stem component 14 and the shell 70 \. The continued movement of the removal tool 150 causes the tabs 80 to move along the annular wall 162 until the shell 70 enters the cavity 166. At which time, the tabs 80 spring back to their full diameter.

Figure 9:
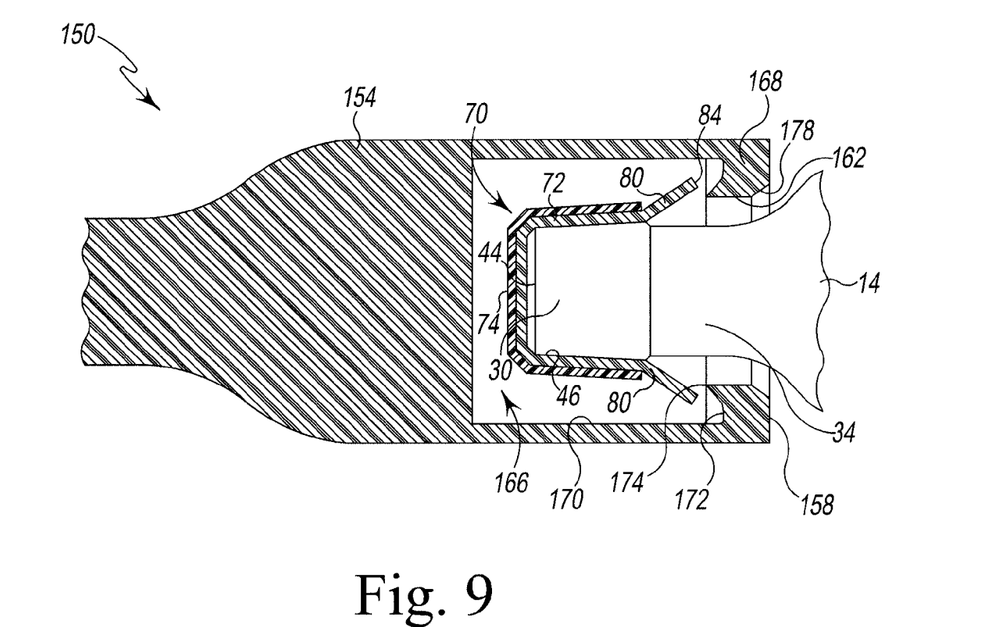
FIG. 9 is a cross-section view of the taper protection system of FIG. 2 showing the protective layer inside of the removal tool.

As shown in FIG. 9, the cavity 166 is sized to receive the trunnion 30 with the shell 70 positioned thereon. In particular, the cavity 166 is sized such that the each distal tip 84 of the shell 70 advances completely past the collar 168. In the illustrative embodiment, the cavity 166 is sized such that each distal tip 84 of the shell 70 advances past the inner edge 174 of the collar 168.

Figure 10:
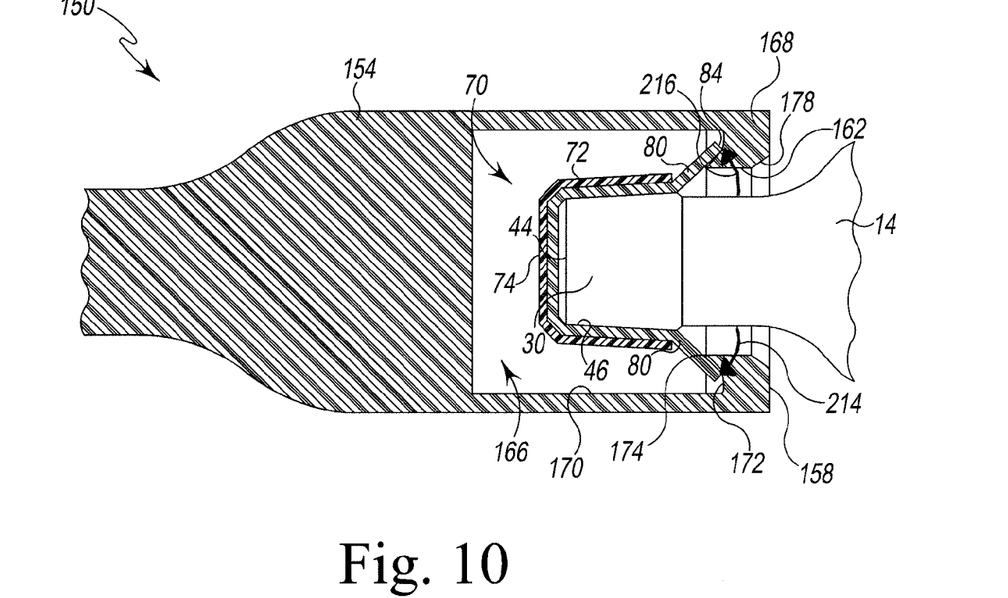
FIG. 10 is a cross-section view of the taper protection system of FIG. 2 showing one or more tabs of the frame in contact with an inner wall of the removal tool.

After the trunnion 30 and the shell 70 are inside of the cavity 166, the removal tool 150 is pulled away from the stem component 14 (as indicated by the arrows 214, 216) such that the distal tips 84 of the tabs 80 engage with the collar 168 of the surgical instrument 150. As shown in FIG. 10, the continued movement of the removal tool 150 causes the distal tabs 80 to deflect outwardly along the conical surface 176 and engage the inner wall 172. The continued movement of the removal tool 150 and the engagement of the tabs 80 with the collar 168 causes the rest of the shell 70 to deflect outwardly and detach from the tapered trunnion 30. In particular, the removal tool 150 applies a force on the distal tabs 80 as indicated by arrows 214, 216, causing the frame 72 to deflect away from the outer surface 46 of the trunnion 30 and detach the entire shell 70 from the trunnion 30.

Figure 11:
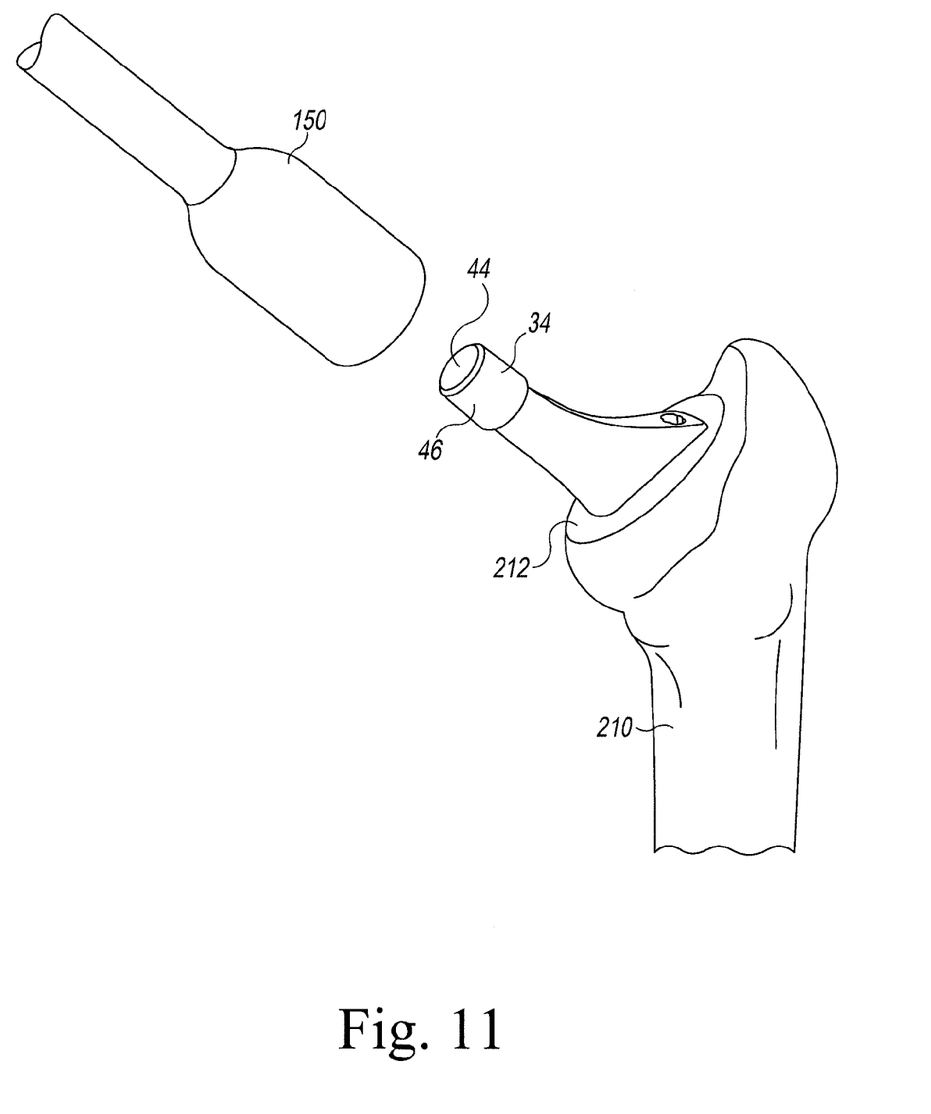
FIG. 11 is a perspective view of taper protection system of FIG. 2 showing the protective layer removed by the removal tool from the tapered stem.

As shown in FIG. 11, after the removal tool 150 has been pulled off of the implanted stem component 14, the trunnion 30 of the stem component 14 is exposed, and the shell 70 remains inside the cavity 166. After the removal of the shell 70 from the stem component 14, the trunnion 30 may be prepared to receive a femoral head component 12.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic hip prosthesis system comprising:
   a femoral head component configured to articulate with a natural or prosthetic acetabulum of a patient, the femoral head component having a tapered bore formed therein,
   a femoral stem component having a tapered trunnion configured to be received in the tapered bore of the femoral head component, and
   a shell positioned over the tapered trunnion of the femoral stem component, the shell including (i) a frame extending over the tapered trunnion, and (ii) a protective coating applied to the frame and the tapered trunnion,
   wherein the frame is formed from a first material and the protective coating is formed from a second material different from the first material,
   wherein the first material is a plastic, and the second material is a biocompatible wax.

2. The orthopaedic hip prosthesis system of claim 1, wherein the femoral stem component includes an elongated body extending to a distal tip and a neck extending superiorly and medially from a proximal end of the elongated body, and the tapered trunnion extends from the proximal end of the neck.

3. The orthopaedic hip prosthesis system of claim 2, wherein the tapered trunnion includes a tapered outer surface that extends from a proximal surface to a distal edge connected to the proximal end of the neck, and the shell extends over the entire tapered outer surface.

4. The orthopaedic hip prosthesis system of claim 1, wherein the frame is a unitary plastic body shaped to conform to the tapered trunnion.

5. The orthopaedic hip prosthesis system of claim 4, wherein the body of the frame comprises a base configured to engage a proximal surface of the tapered trunnion, and a plurality of arms extending from the base along a tapered outer surface of the tapered trunnion.

6. The orthopaedic hip prosthesis system of claim 5, wherein the shell further includes a tab extending outwardly from a distal end of each arm away from the tapered trunnion.

7. The orthopaedic hip prosthesis system of claim 5, wherein the protective coating completely covers the base and the plurality of arms of the frame.

8. An orthopaedic hip prosthesis system comprising:
a femoral head component configured to articulate with a natural or prosthetic acetabulum of a patient, the femoral head component having a tapered bore formed therein,
a femoral stem component having a tapered trunnion configured to be received in the tapered bore of the femoral head component, and
a shell positioned over the tapered trunnion of the femoral stem component, the shell including (i) a frame extending over the tapered trunnion, and (ii) a protective coating applied to the frame and the tapered trunnion,
wherein the frame is a unitary plastic body shaped to conform to the tapered trunnion, and
wherein the body of the frame comprises a base configured to engage a proximal surface of the tapered trunnion, and a plurality of arms extending from the base along a tapered outer surface of the tapered trunnion.

9. The orthopaedic hip prosthesis system of claim 8, wherein the shell further includes a tab extending outwardly from a distal end of each arm away from the tapered trunnion.

10. The orthopaedic hip prosthesis system of claim 8, wherein the protective coating completely covers the base and the plurality of arms of the frame.

11. An orthopaedic hip prosthesis system comprising:
a femoral head component configured to articulate with a natural or prosthetic acetabulum of a patient, the femoral head component having a tapered bore formed therein,
a femoral stem component having a tapered trunnion configured to be received in the tapered bore of the femoral head component,
a shell positioned over the tapered trunnion of the femoral stem component, the shell including (i) a frame extending over the tapered trunnion, and (ii) a protective coating applied to the frame and the tapered trunnion, and
a surgical instrument configured to detach the shell from the tapered trunnion of the femoral stem component, the surgical instrument including a cavity sized to receive the tapered trunnion with the shell positioned thereon, and a collar adapted to engage a distal end of the shell to detach the shell from the tapered trunnion.

12. The orthopaedic hip prosthesis system of claim 11, wherein the shell includes one or more tabs extending away from the tapered trunnion, and the collar is configured to engage the one or more tabs when the tapered trunnion and the shell are positioned in the cavity.

13. The orthopaedic hip prosthesis system of claim 11, wherein the collar is configured to deflect the shell outwardly from the tapered trunnion when the surgical instrument is pulled away from the tapered trunnion.

14. A system for hip orthopaedic surgery, the system comprising:
a femoral head component configured to articulate with a natural or prosthetic acetabulum of a patient, the femoral head component having a tapered bore formed therein,
a femoral stem component having a tapered trunnion configured to be received in the tapered bore of the femoral head component, the tapered trunnion defining a longitudinal axis,
a shell positioned over the tapered trunnion of the femoral stem component, the shell including (i) a frame extending over the tapered trunnion, (ii) one or more distal tabs extending from the frame away from the tapered trunnion, and (iii) a protective coating applied to the frame and the tapered trunnion, and
a surgical instrument configured to detach the shell from the tapered trunnion of the femoral stem component, the surgical instrument including a cavity sized to receive the tapered trunnion with the shell positioned thereon, and a collar adapted to engage the one or more distal tabs of the shell to detach the shell from the tapered trunnion,
wherein (i) when the surgical instrument is advanced in a first direction along the longitudinal axis of the tapered trunnion, engagement between the collar and the one or more distal tabs of the frame causes the one or more distal tabs to deflect inwardly as the tapered trunnion and the shell are advanced into the cavity, and (ii) when the surgical instrument is advanced in a second direction opposite the first direction when the tapered trunnion and the shell are positioned in the cavity, the engagement between the collar and the one or more distal tabs causes the shell to deflect outwardly and detach from the tapered trunnion.

15. The system of claim 14, wherein the femoral stem component includes an elongated body extending to a distal tip and a neck extending superiorly and medially from a proximal end of the elongated body, and the tapered trunnion extends from the proximal end of the neck.

16. The system of claim 15, wherein the tapered trunnion includes a tapered outer surface that extends from a proximal tip to a distal edge connected to the proximal end of the neck, and the shell extends over the entire tapered outer surface.

17. The system of claim 14, wherein the frame of the shell comprises a base configured to engage a proximal surface of the tapered trunnion, and a plurality of arms extending from the base along a tapered outer surface of the tapered trunnion to corresponding distal ends, and the one or more tabs extend from the distal ends of the plurality of arms.

18. The system of claim 14, wherein the frame is a unitary plastic body shaped to conform to the tapered trunnion.

19. The system of claim 14, wherein the protective coating is formed from a biocompatible wax.

20. A method of performing an orthopaedic surgical procedure, the method comprising:

selecting an orthopaedic hip prosthesis comprising (i) a femoral stem component including a tapered trunnion sized to be received in a tapered bore of a femoral head component and (ii) a shell positioned over the tapered trunnion of the femoral stem component, the shell including a frame extending over the tapered trunnion, one or more distal tabs extending from the frame away from the tapered trunnion, and a protective coating applied to the frame and the tapered trunnion, inserting the femoral stem component into a proximal end of a patient's femur, advancing a surgical instrument over the tapered trunnion and the shell, engaging a collar of the surgical instrument with the one or more distal tabs to deflect the one or more distal tabs inwardly toward the femoral stem component, pulling the surgical instrument away from the femoral stem component such that the engagement between the collar of the surgical instrument and the one or more distal tabs causes the shell to deflect outwardly and detach from the tapered trunnion, and securing the femoral head component to the tapered trunnion of the femoral stem component.

* * * * *